United States Patent [19]

Gunderson

[11] Patent Number: 5,734,088

[45] Date of Patent: Mar. 31, 1998

[54] APPARATUS FOR MEASURING STATIC FRICTION PROPERTIES

[76] Inventor: Dennis E. Gunderson, 2008 Greenway Cross #3, Madison, Wis. 53713

[21] Appl. No.: 769,752

[22] Filed: Dec. 20, 1996

[51] Int. Cl.⁶ .................................................. G01N 19/02
[52] U.S. Cl. .................................................. 73/9
[58] Field of Search .................. 73/9, 10, 7, 841

[56] References Cited

U.S. PATENT DOCUMENTS

| 2,471,423 | 5/1949 | Gisser | 73/9 |
| 2,887,874 | 5/1959 | Mason | 73/9 |
| 5,097,696 | 3/1992 | Le Compagnon | 73/9 |

Primary Examiner—Robert Raevis
Attorney, Agent, or Firm—William J. Connors

[57] ABSTRACT

An apparatus for measuring the static friction properties of materials. The apparatus has a means for applying shear force to a sled and table interface in a smooth and repeatable manner. The apparatus operates without operator interference in terms of placing a load on the material to be tested. The apparatus contains a shear type load cell which operates at the same location in the apparatus at which the shear force is applied to a contact interface and at which static friction is generated.

10 Claims, 2 Drawing Sheets

APPARATUS FOR MEASURING STATIC FRICTION PROPERTIES

BACKGROUND

Instruments for measuring the maximum static friction force which can exist between two horizontal surfaces are well known in the art. Most often these instruments comprise a sled of known weight (to which a test piece of specimen material may be attached), a horizontal table (on which a second test piece of specimen material may be affixed), means to create a shearing motion at the interface between sled and table, and means to continuously measure the magnitude of the shearing force applied to the interface.

A test sequence is begun by placing the sled in contact with the table. The motion-creating means is then engaged. The motion-creating means develops a shearing force at the static interface between sled and table, i.e. tends to cause sliding of the sled relative to the table. (In practice it makes little difference which component is stationary and which moves.) So long as the shearing force is less than the maximum static friction value for the materials in contact, the sled and table remain in static contact, i.e. do not slide with respect to each other. As the shearing force increases, however, sliding cannot be indefinitely resisted by the friction force. The maximum static friction value is the shear force at which sliding begins.

Despite the apparent simplicity, experience with such apparatus (in the measurement of the static friction of paper surfaces) is that the static friction values measured are very inconsistent; varying both from one instrument to the next, and from one operator to another using the same instrument. Recent research has shown that results are effected by (a) the "smoothness" of the increasing force profile, and (b) the way in which the operator places and positions the sled on the table. In the first instance, "roughness" and/or vibration in the applied force can cause table and sled to slide relative to each other at a "low" shear force. In the second instance, repositioning of the sled on the table prior to conduct of the test has been shown to significantly elevate the static friction value.

The present invention teaches two novel methods/designs which can serve to significantly improve the consistency of the static friction measurement. The first, is a low-cost force generating means which produces an entirely smooth force profile, free of the shocks, noise and vibration inherent in many other methods. The second is a novel, and effective means for placing the sled on the table in a way which removes the operator as a variable in this sensitive part of the test process, and precludes "repositioning" of the sled after placement.

DESCRIPTION OF THE INVENTION

Means for generating the horizontal shear force

Figure 1:
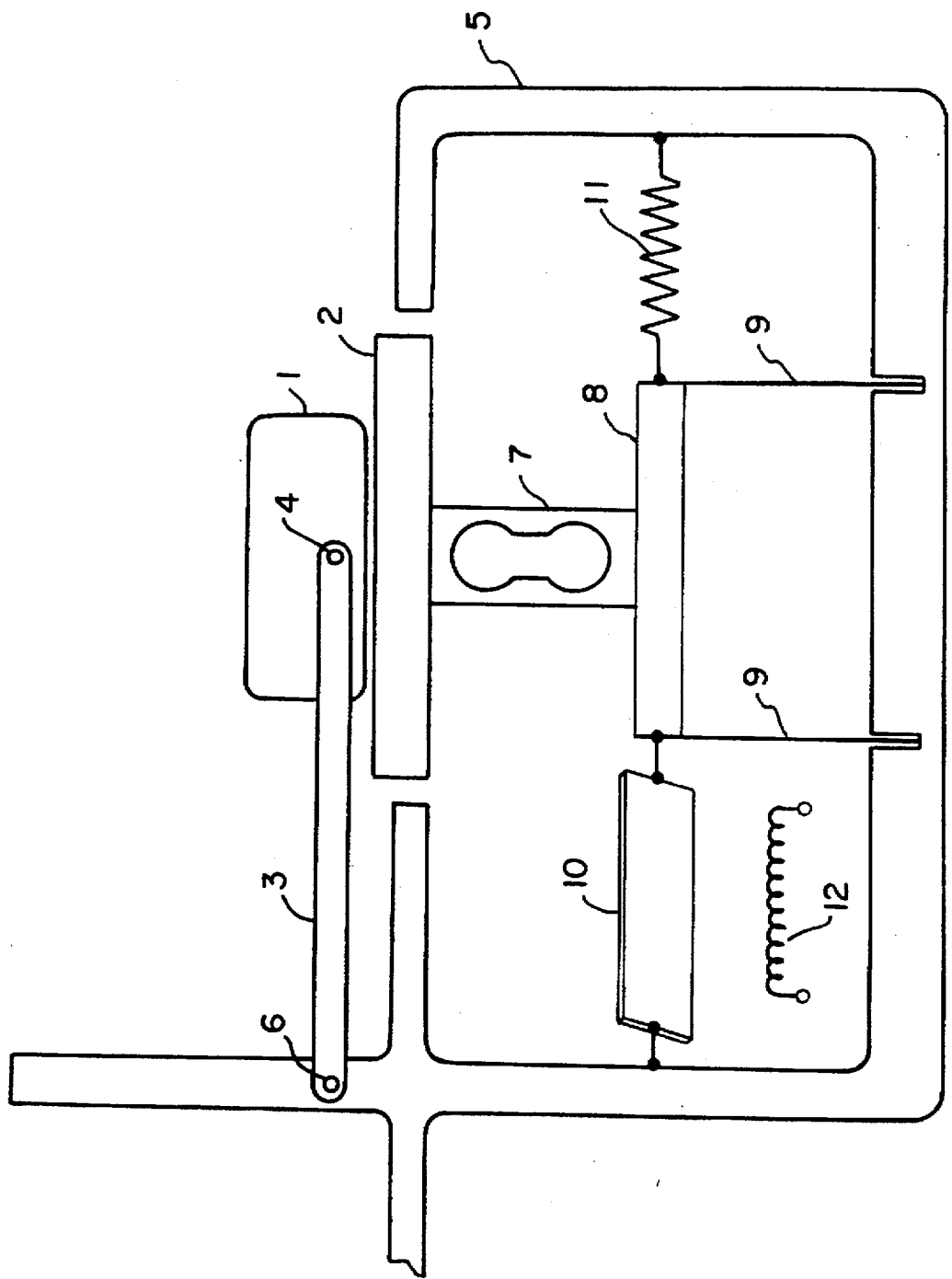
FIG. 1 is a schematic representation of a static friction measurement apparatus.

FIG. 1 is a schematic representation of a static friction measurement apparatus incorporating novel means for creating a smooth, gradually-increasing shear force at the friction surface at the interface of the sled (1) and the table (2). For the sake of simplicity in this discussion the friction surfaces in contact are taken to be the bottom of the sled (1) and the top surface of the table (2). It is obvious that sheet materials of various types can be attached to the sled and table respectively to create different friction surfaces. In FIG. 1 the sled (1) is shown resting on the table (2). Link (3) is connected to the sled (1) at pivot (4) and to the frame (5) at pivot (6). Pivot (4) is located as close as practicable to the friction surface between sled (1) and table (2). Pivot (6) is located so that link (3) is parallel to the surface of the table (2) when the sled (1) is in contact with the table (2).

The table (2) is fixedly attached to a shear-type, strain-gage, load cell (7) located beneath the table. The load cell (7) is fixedly attached to a horizontal plate (8) which is in turn supported by flexible, steel columns (9) which are rigidly attached at one end to plate (8), and at their other end to the frame (5). The load cell (7) is constructed (by means well known in the art) to be sensitive only to forces applied in the horizontal plane. Located, as it is, in direct connection with the table (2) it responds to the full horizontal shear force in the plane of the table, and only the horizontal shear force in the plane of the table.

The displacement required to develop a controlled, slowly-increasing, shear force at the plane where the sled (1) and table (2) are in contact is produced by the thermal expansion of a metal foil strip (10). The foil strip (10) is connected between the frame (5), and the left end of plate (8). A tension spring (11) is connected between the frame (5) and the right end of plate (8). The foil strip (10) is thus held taut under the tension of spring (11). A lamp (12), or other electrically-powered, radiant heating device, is located in close proximity to the metal-foil strip. When the lamp (12) is energized, the metal foil strip is gradually heated. As its temperature increases its length increases, thereby allowing the plate (8) to move gradually to the right under the force of the tension spring (11).

It should be apparent that as the plate (8), load cell (7) and table (2) attempt to move horizontally to the right, relative to the sled (1), which is prevented from moving horizontally by the arm (3), a horizontal shear force is developed at the interface between the sled (1) and the table (2). This horizontal shear force is carried by the static friction between surfaces of the sled (1) and the table (2).

The dimensions and physical properties of the foil strip (10) and operating characteristics of the lamp (12) are selected to achieve suitable rates and amounts of thermal expansion. It is significant in this design that because the controlling element is linear thermal expansion of a single metal element, and because the resulting motion involves only the elastic deformation of metal components, the force produced at the friction surface between sled (1) and table (2) is absolutely smooth and free from vibration.

Means for placing the sled on the table

Figure 2:
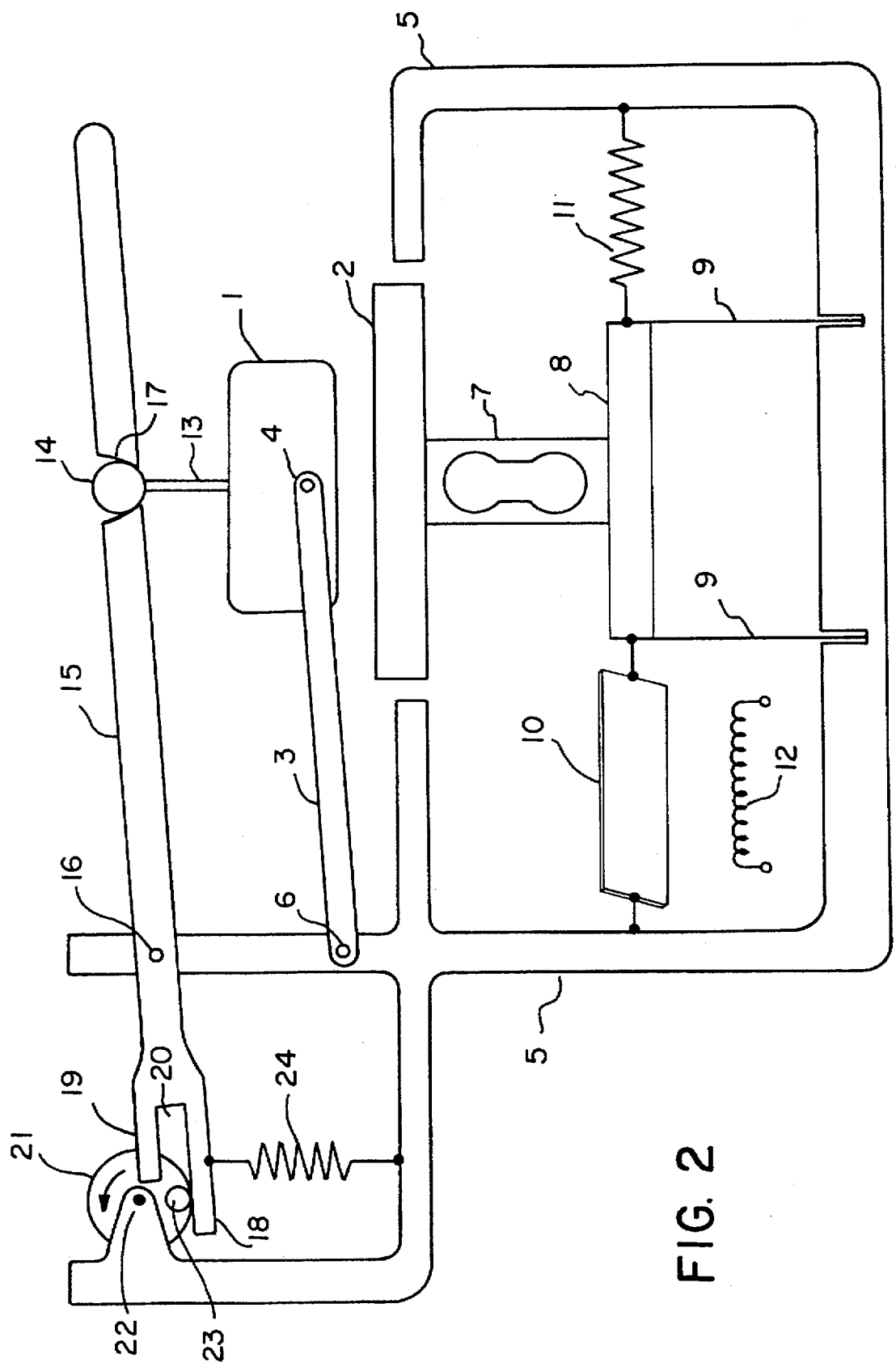
FIG. 2 depicts the apparatus of FIG. 1 augmented with a novel mechanism for automatically lifting and placing the sled on the table.

FIG. 2 depicts the apparatus of FIG. 1 augmented with a novel mechanism for automatically lifting and placing the sled (1) on the table (2) in a controlled, repeatable manner. In FIG. 2 a vertical stem (13) with ball (14) are shown rigidly connected to the top of the sled (1). A lift-arm (15) is pivotably attached to the frame (5) at pivot (16). To the right side of the pivot (16) a ball-socket (17) has been formed in the lift-arm (15). The ball (14) rests in the ball-socket (17), thereby supporting the sled (1) above the surface of the table (2).

The distance from the center of pivot (16) to the center of the ball-socket (17) is the same as that from the center of pivot (6) to the center of pivot (4). The vertical distance from the center of pivot (6) to the center of pivot (16) is the same as the vertical distance from the center of pivot (4) to the center of the ball-socket (17). Consequently the construction comprising the lift-arm (15), arm (3), frame (5), and assembly comprising sled (1), stem (13) and ball (14), acts as a parallel linkage. The lower face of the sled (1), therefore, remains parallel to the upper face of the table (2) regardless of the position of the lift arm or the height of the sled (1) above the table (2).

To the left side of the pivot (16) the lift-arm (15) has a forked construction creating a lower tine (18), upper tine (19) and slot (20). A motor-driven wheel (21) is rotationally fixed, at its center, to the frame (5) at pivot (22). A load-bearing pin (23) is fixedly attached to the wheel (21) at a location displaced from the center. A tension spring (24) is connected to the lift-arm (15) at one end and to the frame (5) at the other end.

When the lift-arm (5) is in the position depicted in FIG. 2, the tension in the spring (24) does not fully offset the clockwise moment imposed on lift-arm (15) by the weight of the sled (1) and other components carried at the ball (14) resting in socket (17). The contact between pin (23) and lower tine (18) provides the additional force needed to hold the sled (1) above the level of the table (2).

To lower the sled (1) onto the surface of the table (2), the motor-driven wheel (21) is rotated counter-clockwise. As the pin (23) moves in a circular path around pivot (22) the pin (23) enters the slot (20) and gradually allows the lift-arm (15) to rotate in a clockwise direction, thereby lowering the sled (1) into contact with the table (2).

Once the sled (1) is resting on the surface of the table, further counter-clockwise rotation of the motor-driven wheel (21) will cause the pin (23), in slot (20), to push upward against the lower surface of tine (19). As pin (23) lifts against tine (19), lift-arm (15) will rotate further in a clockwise direction. In so doing, the ball-socket (17) of lift-arm (15) will become disengaged from ball (14) and stem (13). Thus the sled (1) will be freed from all contact with the lift mechanism. The sled (1) will then be resting under its own weight on the surface of the table (2), and the friction test may proceed.

It should be apparent that when the friction test is complete, the sled may be returned to the "raised" position (as shown in FIG. 2) by reversing the direction-of-rotation of the motor-driven wheel. It should also be apparent that when the sled (1) is in the raised position, it may be raised further by manually lifting the free end of lift-arm (15).

Preferred Embodiment for Measuring the Static Friction Properties of Paper-on-Paper In the embodiment preferred for the measurement of the static friction of paper against paper, one test piece of the specimen paper material is affixed to the lower surface of the sled (1), and a second piece of the specimen paper material is affixed to the top surface of the table (2). The paper test pieces may be of any convenient size which is larger than the contact area between sled and table. The length and width of the sled are approximately 60 millimeters each,—creating a contact area with the table of 3600 square millimeters. The mass of the sled is 800 grams so that when it rests upon the table it pushes down on the table with a force of 7.85 newtons.

For the vast majority of common papers, the shear force required to initiate sliding between two paper surfaces is from 10% to 70% of the force which is applied perpendicular to the surfaces in contact. In the preferred embodiment for paper, therefore, the maximum shearing force which must be developed is nominally 0.8 to 5.5 Newtons.

Because the shear force is transmitted by means of the load cell (7), and must be measured by the load cell (7), the load cell is designed to have a working range of at least 0 to 10 Newtons. Typically, such a load cell, of the shear beam design pictured in FIGS. 1 and 2 is constructed of either aluminum or steel, and has a nominal cross-section of 15×15 millimeters, and a height of 60 to 80 millimeters. A portion of the center part of the cell is removed to achieve the desired elastic deformation under load. Electrical resistance strain gages bonded to the cell translate mechanical deformation to an electrical signal which can be precisely measured. In such a load cell, the electrical signal generated is linearly related to the shear deflection of the cell. A cell of the general configuration described above will deform approximately 0.1 to 0.3 millimeters under full load. Thus, the load cell functions mechanically as a stiff spring, deforming proportional to load at a load-rate of approximately 50 to 100 Newtons per millimeter of deformation.

An example of a commercially available cell of this type is the Model Z6FD1 manufactured by Hottinger Baldwin Messtechnik GMBH of Darmstadt Germany.

In the method taught in the present invention, the end of the load cell (7) which is attached to the table (2) is stationary with respect to the frame (5) so long as static friction is maintained between the sled (1) and the table (2). The controlled deflection required to gradually increase the force transmitted by the load cell is created by the thermal expansion of the metal foil strip (10).

In the preferred embodiment for measuring the static friction of paper against paper, the metal foil strip (10) is of aluminum. It's length, width and thickness are nominally 100, 10 and 0.1 millimeters respectively. The coefficient of linear thermal expansion for aluminum is 0.0000224 millimeters per millimeter of length, per degree centigrade temperature rise. Strip (10), with a length of 100 millimeters, will extend 0.0024 millimeters in length for each degree of temperature rise. A desired 0.1 millimeters of deformation can be a achieved with approximately 50 degrees rise in temperature.

The rate at which the strip (10) heats, and thus expands, is a function of its mass, its radiant absorption properties, and the radiant power and location of the lamp (12). In the preferred embodiment we employ a common, 75 watt, incandescent lamp source—and achieve a 50 degree temperature rise in the strip (10) within approximately 3 to 4 seconds.

The four flexible columns (9) which support plate (8) are made of spring steel. Their cross section is nominally 0.3×10 millimeters; their length 40 millimeters. They hold plate (8) at all times parallel to the bottom surface of the frame (5), but, through flexure of the columns, readily permit small horizontal displacements of plate (8).

Spring (11) is a common steel-wire coil spring with a spring load-rate of nominally 1.5 Newtons per millimeter of extension. In the preferred embodiment, spring (11) is always under tension, producing a relatively constant "pull" at plate (8) of nominally 20 Newtons.

Prior to the start of a friction test, all of the tension force of spring (11) is "carried" as tension in the foil strip (10). During a friction test, however, a portion of that force is gradually transferred to the load cell (7) thereby creating a shear force at the interface between the sled-mounted paper test piece and the table-mounted paper test piece.

A static friction test can begin when the paper test pieces are properly affixed to sled (1) and table (2), and the sled (1) is resting on the table (2). Initially there is no shear force applied to the load cell (7), and consequently no shear force applied to the friction surface between the two paper test pieces. When lamp (12) is energized, however, the foil strip (10) begins to expand, allowing spring (1) to pull plate (8) to the right. The motion of the plate (8) to the right under the tension of spring (11) deforms the load cell and causes a shear force to be transmitted via load cell (7) to the interface between the table (2) and the sled (1). That shear force is carried by the friction force between the surfaces of the two paper testpieces. The shear force is measured by the load cell (7) and continuously recorded or monitored. As the foil strip continues to heat, and therefore expand, plate (8) continues to move very slightly to the right. In this way increasingly greater shear force is created at the interface between the interface between sled (1) and table (2).

At some point, the shear force reaches the maximum friction force which can be sustained under static conditions between the contact surfaces of the paper testpieces. At that instant, the table (2) and its affixed paper test piece will begin to slide to the right under the force of the load cell (7). The test is then complete. The static friction force is recorded as the maximum shear force measured by the load cell (7) prior to sliding of table (2) relative to sled (1).

What is claimed is:

1. An apparatus for measuring the maximum static friction of materials, said apparatus comprising:

(a) A frame with a sled and table movably mounted thereon;
   (b) A parallel linkage lifting and placing means movably mounted on said frame between said frame and said sled for lifting and placing said sled into contact with said table to form a contact interface between said sled and said table,
   (c) A shear force generating means movably mounted on said frame between said frame and said table, said generating means providing a smooth, gradually increasing shear force at said sled and table contact interface through said table,
   (d) A measurement means for measuring said shear force at said contact interface, said measurement means being fixedly mounted between said generating means and said table; wherein said measurement means provides a shear force value at said contact interface, said value being directly proportional to the maximum static friction value of the material mounted at said contact interface.

2. An apparatus according to claim 1, wherein said sled and said table are in parallel, horizontal relationship with each other at said contact interface.

3. An apparatus according to claim 1, wherein said lifting and placing means operates automatically.

4. An apparatus according to claim 1, wherein said force generating means further comprises a plate movably mounted on said frame between said frame and said table, and an expansion means fixedly mounted to said frame between said frame and said plate, whereby expansion of said expansion means provides a smooth, gradually increasing shear force to said table through said plate.

5. An apparatus according to claim 4, wherein said expansion of said expansion means is in response to an energy source operating thereupon.

6. An apparatus according to claim 5, wherein said expansion means is an aluminum strip and said energy source is an incandescent bulb.

7. An apparatus according to claim 1, wherein said measurement means comprises an apparatus for measuring horizontal displacement of said table with respect to said plate.

8. An apparatus according to claim 7, wherein said horizontal displacement is directly proportional to said maximum friction value of said material mounted at said contact interface.

9. An apparatus according to claim 7, wherein said measurement means comprises a load cell.

10. An apparatus according to claim 1, wherein said shear force generating means and said measurement means operate through said table at said contact interface.

* * * * *